(12) United States Patent
Andersen et al.

(10) Patent No.: US 9,089,154 B2
(45) Date of Patent: Jul. 28, 2015

(54) ENZYME-MODIFIED SOYBEAN PRODUCT

(75) Inventors: Lene N. Andersen, Alleroed (DK); Gitte B. Lynglev, Frederiksberg (DK); Lars L. H. Christensen, Alleroed (DK); Rogerio P. Machado, Santa Catarina (BR)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/383,431

(22) PCT Filed: Jul. 14, 2010

(86) PCT No.: PCT/EP2010/060116
§ 371 (c)(1),
(2), (4) Date: Feb. 6, 2012

(87) PCT Pub. No.: WO2011/006916
PCT Pub. Date: Jan. 20, 2011

(65) Prior Publication Data
US 2012/0128824 A1   May 24, 2012

Related U.S. Application Data

(60) Provisional application No. 61/226,477, filed on Jul. 17, 2009.

(30) Foreign Application Priority Data

Jul. 17, 2009 (EP) ................................ 09165758

(51) Int. Cl.
| | | |
|---|---|---|
| A23K 1/165 | (2006.01) | |
| A23L 1/211 | (2006.01) | |
| A23B 9/28 | (2006.01) | |
| A23J 3/16 | (2006.01) | |
| A23J 3/34 | (2006.01) | |
| A23K 1/14 | (2006.01) | |

(52) U.S. Cl.
CPC .............. *A23L 1/2113* (2013.01); *A23B 9/28* (2013.01); *A23J 3/16* (2013.01); *A23J 3/346* (2013.01); *A23K 1/14* (2013.01); *A23K 1/1656* (2013.01); *C12Y 304/19011* (2013.01)

(58) Field of Classification Search
CPC ........... A23L 1/2113; A23B 9/28; A23J 3/16; A23J 3/346; A23K 1/14; A23K 1/1656; C12Y 304/19011
USPC ..................................................... 426/46, 630
See application file for complete search history.

(56) References Cited

U.S. PATENT DOCUMENTS

| 4,512,973 A | * | 4/1985 | Dennis et al. .............. 424/94.64 |
| 6,960,462 B2 | * | 11/2005 | Sjoeholm et al. ............. 435/221 |
| 2003/0211202 A1 | * | 11/2003 | Miller et al. .................... 426/46 |

FOREIGN PATENT DOCUMENTS

| DK | WO 89-06270 | * | 7/1989 | ............. C11D 3/386 |
| WO | 98/56260 A1 | | 12/1998 | |
| WO | 01/58276 A2 | | 8/2001 | |
| WO | 02/069732 A1 | | 9/2002 | |
| WO | 03/041510 A2 | | 5/2003 | |
| WO | 2008/131008 A2 | | 10/2008 | |

OTHER PUBLICATIONS

TRYP_FUSOX—Protein ID. Protein sequence Search. Apr. 29, 2013.*
Mustakas, Journal of the American Oil Chemists' Society, vol. 48, pp. 815-819 (1971).
Sigma-Aldrich, Products for life science research, p. 1494 (2008).
Walsh et al, Food Research International, vol. 36, pp. 677-683 (2003).

* cited by examiner

*Primary Examiner* — Hamid R Badr
(74) *Attorney, Agent, or Firm* — Elias Lambiris

(57) ABSTRACT

The present invention relates to a method of producing a modified soybean product, such as a modified soybean meal, comprising use of a proteolytic enzyme. The invention further relates to use of a proteolytic enzyme in the production of a feed or feed additive product.

16 Claims, No Drawings

ENZYME-MODIFIED SOYBEAN PRODUCT

CROSS-REFERENCE TO RELATED APPLICATIONS

This application is a 35 U.S.C. 371 national application of PCT/EP2010/060116filed Jul. 14, 2010, which claims priority or the benefit under 35 U.S.C. 119 of European application no. 09165758.5 filed Jul. 17, 2009 and U.S. provisional application no. 61/226,477filed Jul. 17, 2009, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a method of producing a modified soybean product, such as a modified soybean meal, comprising use of a proteolytic enzyme. The invention further relates to use of a proteolytic enzyme in the production of a feed or feed additive product.

BACKGROUND OF THE INVENTION

Soybeans are, primarily, an industrial crop, cultivated for oil and protein. Despite the relatively low oil content of the seed (about 20% on moisture-free basis), soybeans are the largest single source of edible oil and account for roughly 50% of the total oilseed production of the world. With each ton of crude soybean oil, approximately 4.5 tons of soybean meal with a protein content of about 44% is produced. For each ton of soybeans processed, the commercial value of the meal obtained usually exceeds that of the oil. Thus, soybean meal is much more than just a by-product of the oil manufacture. The bulk of soybean meal is used in animal feeds.

However, several of the proteins naturally found in soybeans have been found to exert specific physiological effects, such as inhibition of the proteases in the digestive tract of animals and humans. Soybeans contain two types of so-called trypsin inhibitors. They are respectively known as the Kunitz trypsin inhibitor with a molecular weight in the range of 20,000, and the Bowman-Birk inhibitor which is a much smaller polypeptide in the 8,000 dalton range. Both types consist of a number of differentiable proteins. The amino acid sequence and spatial structure of these proteins have been elucidated.

Ingestion of trypsin inhibitors have several physiological effects, including inhibition of trypsin followed by increased pancreatic secretion. This leads to internal loss of protein to the digestive tube as well as hypertrophy of the pancreas. Therefore, inactivation of these proteins to improve digestibility is highly desirable.

The activity of trypsin inhibitors can be reduced by heat treatment of the soybeans. Such heating, however, may also destroy or reduce the availability of certain heat sensitive amino acids and reduce the nutritional value of soy protein. Also, when proteins are heated in the presence of certain carbohydrates, the sugars will complex with free amino groups resulting in a series of reactions called the Maillard reaction, which is for several reasons not desirable. Therefore, other approaches to reduce the activity of trypsin inhibitors and thus improve soybean nutritional values are being searched for.

In WO01/58276, proteolytic degradation of pure Bowman-Birk and Kunitz trypsin inhibitors was demonstrated. In WO98/56260 and WO03/041510, proteolytic treatment of soy protein material to degrade or deactivate trypsin inhibitors is described. The proteolytic enzymes exemplified in these publications are rather unspecific, and WO98/56260 mentions broad specificity as one of the most important parameters for a proteolytic enzyme to be able to degrade such antinutritional factors.

U.S. Pat. No. 4,512,973 showed inactivation of soy trypsin inhibitor using starfish trypsin 1 and a supplementary proteolytic enzyme. It was shown that hydrolysis with starfish trypsin alone did not inactivate the soy trypsin inhibitor. At least one additional proteolytic enzyme, such as carboxypeptidase B, was needed for inactivation.

One purpose for the present inventors has been to provide new methods for inactivation of soy trypsin inhibitors. Inactivation without excessive heat treatment provides distinct nutritional advantages leading directly to economic benefits.

SUMMARY OF THE INVENTION

The present inventors have surprisingly found that antinutritional soy trypsin inhibitors are efficiently degraded when non-toasted soybean flakes, such as white flakes, are incubated with a fungal trypsin-like protease in an aqueous system. The proteolytic treatment can take place at the natural pH of soybean flakes, i.e., without any pH adjustment. The invention therefore provides an economic and feasible process which can easily be adopted by industry. A soybean product, such as a soybean meal, which has been enzyme-modified according to the invention, is especially useful as a feed or a feed additive product.

The invention therefore provides a method of producing an enzyme-modified soybean product comprising
  a) obtaining soybean flakes;
  b) optionally grinding the soybean flakes; and
  c) treating an aqueous slurry of the soybean flakes or the ground soybean flakes with a microbial proteolytic enzyme having specificity for arginine and/or lysine.

In a preferred aspect, the invention provides a method of producing an enzyme-modified soybean meal comprising
  a) obtaining soybean flakes;
  b) defatting the soybean flakes by solvent extraction;
  c) grinding the defatted soybean flakes to a soybean meal; and
  d) treating an aqueous slurry of the defatted soybean flakes or the soybean meal with a microbial proteolytic enzyme having specificity for arginine and/or lysine;
wherein step c) is performed before or after step d).

In another aspect, the invention provides a soybean meal which:
  a) has a pH in aqueous solution between 6 and 7,
  b) comprises at least 20% carbohydrate of total dry matter,
  c) has an average particle size above 150 micrometer,
  d) has a nitrogen solubility index at pH 6.5 of at least 50%, and
  e) has a degree of hydrolysis of between 0.2 and 3%.

In another aspect, the invention provides the use of such soybean meal as a feed or feed additive.

In yet another aspect, the invention provides for the use of at least one proteolytic enzyme in the production of a feed or feed additive product, wherein the proteolytic enzyme has an identity of at least 70% to amino acids 25-248 of SEQ ID NO: 1.

DETAILED DESCRIPTION OF THE INVENTION

Method of Producing an Enzyme-Modified Soybean Product

In a first aspect, the present invention provides a method of producing an enzyme-modified soybean product comprising
a) obtaining soybean flakes;
b) optionally grinding the soybean flakes; and
c) treating an aqueous slurry of the soybean flakes or the ground soybean flakes with a microbial proteolytic enzyme having specificity for arginine and/or lysine.

Soybean Flakes

Processing of whole soybeans into soybean flakes is widely performed, e.g., in the soybean milling industry, as soybean flakes constitute a very good starting material for oil extraction from soybeans. Such oil extraction may be performed either as a mechanical extraction, in which case the flaking facilitates oil release in the press by decreasing the distance that the oil will have to travel to reach the particle surface. Or it may be performed as a solvent extraction, in which case flaking increases the contact surface between the oilseed tissues and the solvent, and also reduces the distance that the solvent and the extract will have to travel in the process of extraction. It is also believed that flaking disrupts the oilseed cells to some degree and thus makes the oil droplets more available for solvent extraction.

Even though much is gained by reducing the size of the solid soy particles prior to oil extraction, grinding of soybeans to a fine powder before extraction is not feasible. In a solvent extraction process, this would impair the flow of solvent around the particles and would make the separation of the oil from the spent solid extremely difficult. Also in a mechanical extraction process, fine grinding would reduce oil yield and produce a crude oil with a high content of fine solid particles. Instead, the oilseeds are rolled by use of a so-called expander into thin flakes, which typically may have a thickness in the range of 0.2 to 0.35 millimetres. Soybean flakes are thus a widely available material in the soybean industry, and increasing their nutritional value, e.g., for animal feeding, will result in great economic benefits.

In the method of producing an enzyme-modified soybean product according to the present invention, soybean flakes are used as the starting material. Such soybean flakes are subjected to treatment with a microbial proteolytic enzyme having specificity for arginine and/or lysine. The soybean flakes may be treated with the enzyme without having been subjected to oil extraction, in which case they may be referred to as full-fat soybean flakes. Or they may have been subjected to extraction of at least part of the oil, in which case they may be referred to as spent soybean flakes, partially defatted soybean flakes or defatted soybean flakes. In a preferred aspect, the soybean flakes are white flakes. White flakes in the context of the present invention means spent soybean flakes with minimum protein denaturation. White flakes are widely applied in the soybean industry as the starting material for the production of soybean protein isolates, most concentrates and texturized products.

Prior to flaking, the raw soybeans may have been subjected to one or more steps selected among drying, tempering, cleaning, classification, cracking, dehulling and conditioning.

Before step c), the soybean flakes may optionally be ground into finer particles. If such grinding is performed on spent soybean flakes, i.e., the flakes which remain after at least partial removal of the oil by a solvent or mechanical extraction process, the ground flakes may be referred to as a soybean meal. A soybean meal is typically not as finely ground as a soybean flour, which is normally defined as having a size such that the particles can pass through a No. 100 mesh (U.S. standard) screen, or which may even have been very finely ground, so that less than 1% of the flour is retained on a 300 mesh (U.S. standard) screen.

In the method of producing an enzyme-modified soybean product according to the present invention, it may also be that full-fat soybean flakes are ground before enzyme treatment according to step c). But also in this case, the full-fat soybean flakes need not be as finely ground as in the production of a full-fat soybean flour.

However, in the method of producing an enzyme-modified soybean product according to the present invention, the enzyme treatment may also be performed on soybean flakes which have not been ground. In that case, the flakes may optionally be ground after the enzyme treatment. Also, even if the flakes are ground prior to the enzyme treatment, they may be further ground at a later stage.

In a preferred aspect according to the present invention, at least 50% (w/w) of the soybean flakes or the ground soybean flakes to be enzyme treated according to step c) will be retained in a No. 100 mesh (US standard) screen. In another preferred aspect, the soybean flakes or the ground soybean flakes to be enzyme treated according to step c) have an average particle size above 150 micrometer.

In one aspect, the soybean flakes or the ground soybean flakes are subjected to defatting before the enzyme treatment. In another aspect, the soybean flakes or the ground soybean flakes are subjected to defatting after the enzyme treatment. Defatting in the context of present invention means that at least part of the oil is separated (extracted). Preferably, the soybean flakes are subjected to defatting before the optional grinding.

In one aspect, the soybean flakes or the ground soybean flakes are subjected to defatting by solvent extraction before the enzyme treatment. In another aspect, the soybean flakes or the ground soybean flakes are subjected to defatting by solvent extraction after the enzyme treatment. Preferably, the soybean flakes are subjected to defatting by solvent extraction before the optional grinding. The extraction is preferably performed using a non-polar solvent. In a preferred aspect, hexane is used as solvent in the solvent extraction.

After the optional oil extraction, remaining solvent may be removed and potentially recovered from the spent flakes. Today combined desolventizing and toasting is widely applied in the production of soybean meal for animal feeding. This process is one of the most critical operations in oil mill practice, since it determines, to a large extent, the quality of the spent flakes.

The toasting, which is a heat treatment which often involves direct steam, is among others used to inactivate the trypsin inhibitors naturally present in the soybeans. However, as discussed above, excessive heating, in particular excessive heating at a high moisture content, also reduces the nutritional value of soy protein.

In the aspects according to the present invention, which include defatting of the soybean flakes or the ground soybean flakes by solvent extraction before the enzyme treatment, the spent flakes are preferably desolventized without excessive heat treatment in the presence of direct steam. One preferred method of desolventizing with minimum protein denaturation is flash desolventizing. In this process, the solvent laden spent flakes coming out from the extracfor are fluidized in a stream of superheated solvent vapors. The superheat of the vapor provides the energy for the evaporation of solvent from the flakes. The turbulent nature of the flake-vapor flow permits extremely rapid heat and mass transfer. Protein denaturation is minimized, mainly because of the short heating time.

The flash desolventizing is preferably followed by rapid cooling for further preventing undue protein denaturation.

In a preferred aspect according to the present invention, the method of producing an enzyme-modified soybean product includes defatting of the soybean flakes by solvent extraction before the enzyme treatment, wherein the soybean flakes are not subjected to toasting prior to step c). In another preferred aspect, the method of producing an enzyme-modified soybean product includes defatting of the soybean flakes by solvent extraction before the enzyme treatment, wherein the soybean flakes are desolventized by flash desolventizing prior to step c).

In a preferred aspect of the method of producing an enzyme-modified soybean product according to the present invention, the soybean flakes or the ground soybean flakes to be enzyme treated according to step c) have not been heated to a temperature of 70° C. or above in the presence of more than 20% (w/w) water. In a more preferred aspect, the soybean flakes or the ground soybean flakes to be enzyme treated according to step c) have not been heated to a temperature of 68° C. or above, preferably 65° C. or above, in the presence of more than 20% (w/w) water. In an even more preferred aspect, the soybean flakes or the ground soybean flakes to be enzyme treated according to step c) have not been heated to a temperature of 60° C. or above in the presence of more than 20% (w/w) water.

In another preferred aspect, the soybean flakes or the ground soybean flakes have a content of trypsin inhibitor activity before the enzyme treatment according to step c) which results in at least 50% inhibition of trypsin activity at a soy flake concentration of 0.02%, preferably at a soy flake concentration of 0.01%, more preferably at a soy flake concentration of 0.005%, when tested in a residual trypsin inhibitor assay (RIA). The residual trypsin inhibitor assay may be performed as described in Example 1 of the present application.

In a more preferred aspect, the soybean flakes or the ground soybean flakes have a content of trypsin inhibitor activity before the enzyme treatment according to step c) which results in at least 50% inhibition of trypsin activity at a soy flake concentration of 0.02%, preferably at a soy flake concentration of 0.01%, more preferably at a soy flake concentration of 0.005%, when tested in the residual trypsin inhibitor assay (RIA) described in Example 1. For example, the white flakes used in Example 1 of the present application, before being incubated with or without enzyme, have a content of trypsin inhibitor activity which results in 50% inhibition of trypsin activity at a soy flake concentration of 0.002% when tested in the residual trypsin inhibitor assay (RIA) described in Example 1.

In another more preferred aspect, the soybean flakes or the ground soybean flakes have a content of trypsin inhibitor activity before the enzyme treatment according to step c) which results in at least 50% inhibition of trypsin activity at a soy flake concentration of 0.02%, preferably at a soy flake concentration of 0.01%, more preferably at a soy flake concentration of 0.005%, when tested in a trypsin inhibitor assay as follows:
  (i) The sample is diluted in a buffer (25 mM, 0.02% Brij 35, pH 6.5). The concentration after this dilution is the soy flake concentration referred to above.
  (ii) 100 μl of each dilution is mixed with 50 μl 0.001 mg/ml porcine trypsin in the well of a microtiter plate and pre-incubated for 10 minutes.
  (iii) 150 μl trypsin substrate (0.2 mg/ml Boc VLGR-pNA in 25 mM MES, 0.02% Brij, pH 8) is added to each sample and after mixing absorbance at 405 nm is read every 10 seconds for 3 minutes.
  (iv) For each sample, the trypsin activity A is calculated by linear regression from the initial slope of increase in absorbance at 405 nm.
  (v) A sample with 100 μl buffer without soybean flakes is included to give trypsin activity without inhibitor, Amax, and another sample with water added instead of trypsin is included to give background activity, Amin.
  (vi) Inhibition of trypsin activity is then calculated by:

Inhibition=($A$max–$A$)/($A$max–$A$min)*100%

In another preferred aspect, the protein dispersibility index of the soybean flakes or the ground soybean flakes to be enzyme treated according to step c) is above 30%, preferably above 40% or above 50%, more preferably above 60%, and even more preferably above 70%. Protein dispersibility index may be determined according to Marsman et al., 1995, *Journal of Food Engineering*, 26, pp. 13-28.

In another preferred aspect, the nitrogen solubility index (NSI) of the soybean flakes or the ground soybean flakes to be enzyme treated according to step c) is above 30%, preferably above 40% or above 50%, more preferably above 60%, and even more preferably above 70%. Nitrogen solubility index may be determined according to *Official Methods and Recommended Practices of the American Oil Chemists' Society*, edited by D. Firestone, American Oil Chemists'Society, 1985, Method Ba 11-65.

Soybeans contain urease, the enzyme that converts urea to ammonia. Destruction of the urease enzyme in soybeans by heating is correlated with destruction of trypsin inhibitors. Urease activity is, therefore, often used as an indicator of the degree of soybean processing. Processed soybean material for use in feed which has a urease activity of about 0.2 pH units is normally considered underprocessed, whereas processed soybean material having a urease activity of about 0.01 may be considered overprocessed.

In another preferred aspect of the method of producing an enzyme-modified soybean product according to the present invention, the urease activity of the soybean flakes or the ground soybean flakes to be enzyme treated according to step c) is above 0.4, preferably above 0.5, more preferably above 1, and even more preferably above 1.5, pH units. The skilled person will know how to measure the urease activity. It may be determined according to AOCS (1984), Official Method Ba 9-58.

In another preferred aspect, at least 50% of Kunitz trypsin inhibitor and/or Bowman-Birk inhibitor in the soybean flakes or the ground soybean flakes to be enzyme treated according to step c) are essentially non-denatured.

Proteolytic Enzyme

The methods of the present invention involve treatment with a microbial proteolytic enzyme having specificity for arginine and/or lysine. Such microbial proteolytic enzyme to be used according to the invention is an endopeptidase.

By "specificity for arginine and/or lysine" is meant that the proteolytic enzyme has a higher specificity for cleaving on the carboxy terminal side of either arginine or lysine than for cleaving on the carboxy terminal side of any other amino acid. In one aspect, the proteolytic enzyme specifically cleaves on the carboxy terminal side of arginine, meaning that the proteolytic enzyme has a higher specificity for cleaving on the carboxy terminal side of arginine than for cleaving on the carboxy terminal side of any other amino acid. In another aspect, the proteolytic enzyme specifically cleaves on the carboxy terminal side of lysine, meaning that the proteolytic enzyme has a higher specificity for cleaving on the carboxy terminal side of lysine than for cleaving on the carboxy terminal side of any other amino acid.

Typically, the proteolytic enzyme has optimal proteolytic activity at a pH from about 6.0 to about 11.0, preferably at a pH from about 8 to about 10, and at a temperature from about 40° C. to about 70° C., preferably at a temperature from about 45° C. to about 60° C. or from about 45° C. to about 55° C.

A proteolytic enzyme to be used in the method of the invention is of microbial origin. The use of microbial enzymes, rather than animal or plant enzymes, is advantageous in that microbial enzymes exhibit a broad spectrum of characteristics (pH optima, temperature etc.) and may be consistently obtainable in relatively large quantities.

The proteolytic enzyme is preferably a trypsin-like endopeptidase of microbial origin. In the context of the present invention, a trypsin-like endopeptidase is an endopeptidase having a specificity similar to that of trypsin.

In one aspect, the proteolytic enzyme is a bacterial endopeptidase.

In another aspect, the proteolytic enzyme is a fungal endopeptidase. In a preferred aspect, the proteolytic enzyme is from a strain of *Fusarium*, preferably *Fusarium oxysporum*, e.g. having the amino acid sequence of the mature polypeptide of SEQ ID NO: 1 of the present application (SWISSPROT No. P35049). A trypsin-like endopeptidase from *Fusarium oxysporum* having the amino acid sequence shown as amino acids 25-248 of SEQ ID NO: 1 has previously been described (U.S. Pat. Nos. 5,288,627; 5,693,520).

In one aspect, the proteolytic enzyme is a trypsin-like endopeptidase from *Fusarium solani*, e.g. AP977S having the amino acid sequence of the mature polypeptide of SEQ ID NO: 2 of the present application (GENESEQP: ADZ80577). In another aspect, the proteolytic enzyme is a trypsin-like endopeptidase from *Fusarium* sp., e.g. AP971 having the amino acid sequence of the mature polypeptide of SEQ ID NO: 3 of the present application.

In a preferred aspect of the method of the invention, the proteolytic enzyme is selected from the group consisting of:

i) a polypeptide having an amino acid sequence which is at least 60%, 70%, 80%, 85%, 90%, 95% or 98% identical to (A) any of SEQ ID NOs: 1, 2, or 3, or (B) a fragment of any of these sequences having protease activity; and ii) a polypeptide having an amino acid sequence modified by substitution, deletion, and/or insertion of one or several amino acids in (A) any of SEQ ID NOs: 1, 2 or 3, or (B) a fragment of any of these sequences having protease activity.

A fragment of an amino acid sequences having protease activity may be the amino acid sequence of the active enzyme, e.g. after processing, such as after any signal peptide and/or propeptide has been cleaved off. Preferred fragments are amino acids 25-248 of SEQ ID NO: 1, amino acids 26-251 of SEQ ID NO: 2, or amino acids 18-250 of SEQ ID NO: 3.

In one preferred aspect of the method of the invention, the proteolytic enzyme has an amino acid sequence which is at least 60%, 70%, 80%, 85%, 90%, 95% or 98% identical to amino acids 25-248 of SEQ ID NO: 1.

For purposes of the present invention, the alignment of two amino acid sequences can be determined by using the Needle program from the EMBOSS package (Rice, P., Longden, I. and Bleasby, A. (2000) EMBOSS: The European Molecular Biology Open Software Suite. Trends in Genetics 16, (6) pp. 276-277; http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between two amino acid sequences is calculated as the number of exact matches in an alignment of the two sequences, divided by the length of the shortest of the two sequences. The result is expressed in percent identity. An exact match occurs when the two sequences have identical amino acid residues in the same positions of the overlap. The length of a sequence is the number of amino acid residues in the sequence (e.g. the length of SEQ ID NO: 1 is 248 amino acids).

Treatment with Proteolytic Enzyme

In the methods of the present invention, an aqueous slurry of soybean flakes or ground soybean flakes are treated with a microbial proteolytic enzyme having specificity for arginine and/or lysine.

In one aspect, the aqueous slurry of the soybean flakes or the ground soybean flakes has a dry matter content of at least 10%, preferably at least 15% or at least 20%, and more preferably at least 25% or at least 30%. In another aspect, the aqueous slurry of the soybean flakes or the ground soybean flakes has a dry matter content of at least 35%, such as at least 40%.

It is to be understood, that the term aqueous slurry includes slurries having a high dry matter content, which may also be termed an aqueous paste.

The proteolytic enzyme may be added to the aqueous slurry to start the enzyme treatment, or the aqueous slurry may be prepared by mixing the enzyme with water and adding this to the soybean flakes or the ground soybean flakes.

The amount of proteolytic enzyme added to the soybean flakes or the ground soybean flakes may range from about 1 mg to about 5000 mg enzyme protein per kilogram dry matter, preferably from 10 mg to about 1000 mg enzyme protein per kilogram dry matter, more preferably from about 50 mg to about 1000 mg enzyme protein per kilogram dry matter, and even more preferably from about 50 mg to about 500 mg enzyme protein per kilogram dry matter.

The enzyme treatment is performed at a temperature at which the proteolytic enzyme is active; the skilled person will know which temperature to choose. Preferably, the enzyme treatment is performed at a temperature of between 50° C. and 70° C., more preferably at a temperature of between 55° C. and 65° C.

Preferably, the enzyme treatment is performed at the natural pH of the aqueous slurry of the soybean flakes, i.e., without any pH adjustment. In one preferred aspect, the enzyme treatment is performed at between pH 6 and pH 7.

As will be appreciated by a skilled artisan, the duration of the enzyme treatment can and will vary. Generally speaking, the duration of the enzyme treatment may range from a few minutes to many hours, such as, from about 10 minutes to about 5 hours. In one aspect, the enzyme treatment is performed for between 30 minutes and 2 hours. In general, performing the enzyme treatment for a short time may be to prefer, but this needs to be balanced against the amount of enzyme to be added.

In a preferred aspect, the enzyme treatment results in inactivation of at least 50% of Kunitz trypsin inhibitor and/or Bowman-Birk inhibitor in the enzyme-modified soybean product as compared to a similar method without treatment with the proteolytic enzyme.

After completion of the enzyme treatment, the proteolytic enzyme may be inactivated. The skilled person will know how to inactivate the enzyme.

In one aspect, one or more additional enzymes are added either at the same time as the microbial proteolytic enzyme or in separate treatment steps. The skilled person will know whether such treatment with one or more additional enzymes is preferably performed at the same time as the treatment with the microbial proteolytic enzyme or as a separate step, e.g., at a different temperature or at a different pH. Such additional enzymes may be selected among hydrolytic enzymes, such as, e.g., pectinolytic enzymes, cellulolytic enzymes, hemicellulolytic enzymes, phosphorolytic enzymes, other proteolytic enzymes, or combinations thereof. A typical useful phosphorolytic enzyme is a phytase. A useful pectinolytic enzyme may, e.g., be an endo-galactanase or a beta-galactosidase. A typical pectinolytic enzyme may, e.g., be the commercial product Viscozyme® (Novozymes NS). In a preferred aspect, such additional enzyme is a glycosyl hydrolase. In a more preferred aspect, such additional enzyme is an alpha-galactosidase.

Enzyme-Modified Soybean Product

The present invention provides a method of producing an enzyme-modified soybean product.

In one preferred aspect, the enzyme-modified soybean product produced according to the method of the invention comprises at least 20%, preferably at least 25% or at least 30%, and more preferably at least 35% carbohydrate (w/w) of total dry matter.

The proteins in the enzyme-modified soybean product produced according to the present invention are not extensively hydrolysed. In one aspect, the proteins have a size distribution where more than 20% of the proteins (w/w) are bigger than about 10 kDa as measured by gel electrophoresis.

In another preferred aspect, the proteins in the enzyme-modified soybean product produced according to the method of the invention have a degree of hydrolysis of below 5%, preferably below 4% and more preferably below 3%.

The degree of hydrolysis (DH) expresses the extent of the protein hydrolysis obtained by the method. In the context of the invention, the degree of hydrolysis (DH) is defined as follows:

DH=(Number of peptide bonds cleaved/Total number of peptide bonds)×100%

The skilled person will know how to measure the DH. It may, e.g., be done using a method as described in Adler-Nissen, J., 1986, Enzymatic Hydrolysis of Food Proteins, Chapter 5, pp. 122-124.

In another preferred aspect, the protein dispersibility index of the enzyme-modified soybean product is above 30%, preferably above 40% or above 50%, more preferably above 60%, and even more preferably above 70%.

In another preferred aspect, the nitrogen solubility index (NSI) of the enzyme-modified soybean product is above 30%, preferably above 40% or above 50%, more preferably above 60%, and even more preferably above 70%.

In another preferred aspect, the enzyme-modified soybean product has a residual trypsin inhibitor activity which is at least 30% lower than a soybean product produced by a similar method without addition of proteolytic enzyme. Preferably, the enzyme-modified soybean product has a residual trypsin inhibitor activity which is at least 40% lower, more preferably at least 50% lower, and even more preferably at least 60% lower, than a soybean product produced by a similar method without addition of proteolytic enzyme.

In yet another preferred aspect, the enzyme-modified soybean product produced by the method of the present invention is a feed or feed additive.

The invention therefore also provides the use of an enzyme-modified soybean product produced by a method of the present invention as a feed or feed additive. It may be used, e.g., for feed in aquaculture or beef industry, or for feeding dairy cattle, horses, poultry, sheep, and/or pigs.

Method of Producing an Enzyme-Modified Soybean Meal

In a preferred aspect of the method according to the present invention, the soybean flakes are subjected to defatting by solvent extraction before the enzyme treatment, and the spent flakes are ground to a soybean meal before or after the enzyme treatment. The resulting enzyme-modified soybean product may be referred to as an enzyme-modified soybean meal. Thus, in a preferred aspect, the present invention provides a method of producing an enzyme-modified soybean meal comprising a) obtaining soybean flakes;
b) defatting the soybean flakes by solvent extraction;
c) grinding the defatted soybean flakes to a soybean meal; and
d) treating an aqueous slurry of the defatted soybean flakes or the soybean meal with a microbial proteolytic enzyme having specificity for arginine and/or lysine;

wherein step c) is performed before or after step d).

Soybean Meal

In another aspect, the present invention provides a soybean meal which can be obtained by the method of the invention. Thus, the present invention provides a soybean meal which:

a) has a pH in aqueous solution between 6 and 7,
b) comprises at least 20% carbohydrate of total dry matter,
c) has an average particle size above 150 micrometer,
d) has a nitrogen solubility index at pH 6.5 of at least 50%, and
e) has a degree of hydrolysis of between 0.2 and 3%.

In a preferred aspect, the soybean meal has a urease activity which is below 0.2, preferably below 0.1, more preferably below 0.05, pH units.

In another preferred aspect, the soybean meal comprises at least 25%, preferably at least 30%, and more preferably at least 35% carbohydrate (w/w) of total dry matter.

In another preferred aspect, the nitrogen solubility index (NSI) of the soybean meal is above 60%, preferably above 70%.

Use of a Proteolytic Enzyme in the Production of Feed

In a third aspect, the present invention provides for the use of at least one proteolytic enzyme in the production of a feed or feed additive product, wherein the proteolytic enzyme has an identity of at least 70% to amino acids 25-248 of SEQ ID NO: 1.

In a preferred aspect, such proteolytic enzyme is a microbial proteolytic enzyme, preferably a fungal proteolytic enzyme. In a more preferred aspect, such proteolytic enzyme is from a strain of *Fusarium*, preferably, *Fusarium oxysporum*.

In a preferred aspect, such proteolytic enzyme has specificity for arginine and/or lysine.

In another preferred aspect, such proteolytic enzyme is a trypsin-like endopeptidase.

In a preferred aspect, such proteolytic enzyme has optimal proteolytic activity at a pH from about 6.0 to about 11.0, preferably at a pH from about 8 to about 10, and at a temperature from about 40° C. to about 70° C., preferably at a temperature from about 45° C. to about 60° C. or from about 45° C. to about 55° C.

In a preferred aspect, such proteolytic enzyme has an amino acid sequence which is at least 80%, preferably at least 85%, more preferably at least 90%, even more preferably at least 95%, and most preferably at least 98%, identical to amino acids 25-248 of SEQ ID NO: 1.

EXAMPLES

Example 1

Residual Trypsin Inhibitor Analysis (RIA) on White Flakes (WF) Treated with Trypsin-Like Endopeptidase from *Fusarium oxysporum* (Prot1)

Enzyme (trypsin-like endopeptidase from *Fusarium oxysporum*) corresponding to a final concentration of 100, 250, 500 and 1000 mg ep/kg white flakes, respectively, was mixed into 19.2 ml and 63.5 ml milli-Q water, respectively—the enzyme mixture were added to 25 g of white flakes. Final concentration of dry-matter (dm) white flakes was 50% and 25% w/w, respectively. The 25% w/w dm white flakes slurries were further mixed by manual mixing with a spoon, the 50% slurries were of practical reasons further mixed by use of blender (Braun Multiquick professional MR 5550 BC-HC). A control without enzyme added was included for each treatment. No pH adjustment took place.

The samples were incubated in a water-bath at 55, 60 and 65° C. for 60 min.

The soy samples were transferred into plastic tubes and kept in a freezer for later residual trypsin inhibitor analysis.
Materials:

The enzyme used is the mature fungal trypsin-like endopeptidase from *Fusarium oxysporum*, Prot1. The amino acid sequence (translation product) of such endopeptidase is shown as SEQ ID NO: 1 of the present application.

White Flakes, non heat treated; 11.5% moisture, approx. 50% protein content, approx. 30% carbohydrate.
RIA Analysis:

To determine the residual trypsin inhibitor activity, the soy suspension was diluted (500×, 1000× and 2000×) with a buffer (25 mM MES, 0.02% Brij, pH 6.5). 100 µl of the dilution was then mixed with 50 µl porcine trypsin (0.001 mg/ml) in the well of a microtiter plate. After 10 min pre-incubation (to assure equilibrium binding between porcine trypsin and soy trypsin inhibitors), 150 µl trypsin substrate (Stock solution: 50 mg/ml Boc-VLGR-pNA in DMSO. Substrate solution: 4 µl stock solution per ml buffer (0.1 M Tris, 0.02% Brij 35, pH 8.0)) was added and after mixing absorbance at 405 nm was read every 10 seconds for 3 minutes in a Spectramax Plus spectrophotometer. Trypsin activity was calculated from the initial slope of increase in absorbance at 405 nm by linear regression. A well with 100 µl buffer instead of soy dilution was also included to give trypsin activity without inhibitor.

It has been verified that the contribution from Prot1 on the measured trypsin activity was negligible.

The measured trypsin activity as function of soy concentration was fitted to the expression:

$$A = (A\max - A\min)/(1 + (\log(I50)/\log(C))^{\text{Slope}}) + A\min$$

where A is the measured activity, Amax is the maximal activity given by the well without soy added, Amin is the background activity when no trypsin is added, I50 is the soy concentration that inhibits the trypsin activity by 50% and C is the soy concentration. I50 is calculated for each sample using a least squares fit and the residual inhibitor activity (RIA) level is calculated from:

$$\text{RIA} = I50(\text{sample})/I50(\text{reference}) * 100\%$$

where I50(sample) is the calculated I50 for the sample and I50(reference) is the I50 calculated for a soy sample without protease added.

Results/Conclusion:

TABLE 1

Residual inhibitor activity as function of enzyme addition, dry matter content (dm), temperature

| Enzyme dosage | % w/w dm WF | Temp ° C. | Reaction time | % RIA |
|---|---|---|---|---|
| WF (control) | 50 | 55 | 60 min | 100 |
| 100 mg ep/kg | 50 | 55 | 60 min | 88 |
| 250 mg ep/kg | 50 | 55 | 60 min | 77 |
| 500 mg ep/kg | 50 | 55 | 60 min | 80 |
| 1000 mg ep/kg | 50 | 55 | 60 min | 79 |
| WF (control) | 25 | 55 | 60 min | 100 |
| 100 mg ep/kg | 25 | 55 | 60 min | 65 |
| 250 mg ep/kg | 25 | 55 | 60 min | 54 |
| 500 mg ep/kg | 25 | 55 | 60 min | 62 |
| 1000 mg ep/kg | 25 | 55 | 60 min | 60 |
| WF (control) | 50 | 60 | 60 min | 100 |
| 100 mg ep/kg | 50 | 60 | 60 min | 85 |
| 250 mg ep/kg | 50 | 60 | 60 min | 73 |
| 500 mg ep/kg | 50 | 60 | 60 min | 80 |
| 1000 mg ep/kg | 50 | 60 | 60 min | 55 |
| WF (control) | 25 | 60 | 60 min | 100 |
| 100 mg ep/kg | 25 | 60 | 60 min | 47 |
| 250 mg ep/kg | 25 | 60 | 60 min | 47 |
| 500 mg ep/kg | 25 | 60 | 60 min | 34 |
| 1000 mg ep/kg | 25 | 60 | 60 min | 26 |
| WF (control) | 50 | 65 | 60 min | 100 |
| 100 mg ep/kg | 50 | 65 | 60 min | 90 |
| 250 mg ep/kg | 50 | 65 | 60 min | 73 |
| 500 mg ep/kg | 50 | 65 | 60 min | 70 |
| 1000 mg ep/kg | 50 | 65 | 60 min | 61 |
| WF (control) | 25 | 65 | 60 min | 100 |
| 100 mg ep/kg | 25 | 65 | 60 min | 100 |
| 250 mg ep/kg | 25 | 65 | 60 min | 59 |
| 500 mg ep/kg | 25 | 65 | 60 min | 37 |
| 1000 mg ep/kg | 25 | 65 | 60 min | n.d. |

As can be deduced from Table 1, effects of protease treatment of white flakes on RIA are observed for all treatments including enzymes. RIA values were dependant on enzyme concentration, white flakes concentration and temperature. At 60° C. and 25% dm white flakes, RIA reduction above 50% were obtained at all enzyme dosages, while high white flakes content or temperatures above or below 60° C. affects the efficiency of the enzyme.

Example 2

Residual Trypsin Inhibitor Analysis (RIA) on White Flakes (WF) Treated with Combination of Trypsin-Like Endopeptidase from *Fusarium oxysporum* (Prot1) and Alpha-Galactosidase Enzyme corresponding to a final concentration of 1000 mg endopeptidase ep/kg white flakes and 47 mg alpha-galactosidase ep/kg white flakes were mixed into 77 and 254 g milli-Q water respectively—the enzyme mixtures were added to 100 g of white flakes. The slurries were further mixed by manual mixing with a spoon. A control without enzyme added was included for each treatment. No pH adjustment took place. Final concentration of dry-matter white flakes was 50% and 25% w/w respectively.

The samples were incubated in a water-bath at 50, 60 and 65° C. for 60 and 120 minutes respectively.

The soy samples were transferred into plastic tubes and kept in a freezer for later residual trypsin inhibitor analysis.
Materials:

Alpha-galactosidase from *Aspergillus niger* described in EP692024B1

Trypsin-like endopeptidase from *Fusarium oxysporum*, Prot1 (same as in Example 1)

White Flakes, non heat treated; 11.5% moisture, approx. 50% protein content, approx. 30% carbohydrate
RIA Analysis:
RIA analyses were performed as in Example 1.
Results/Conclusion:

TABLE 2

Residual inhibitor activity as function of enzyme addition, dry matter content (dm), temperature and time

| Enzyme dosage | % w/w dm WF | Temp ° C. | Reaction time | % RIA |
|---|---|---|---|---|
| WF (control) | 50 | 50 | 60 min | 100 |
| Prot1/A-gal | 50 | 50 | 60 min | 84 |
| WF (control) | 25 | 50 | 60 min | 100 |
| Prot1/A-gal | 25 | 50 | 60 min | 53 |
| WF (control) | 50 | 60 | 60 min | 100 |
| Prot1/A-gal | 50 | 60 | 60 min | 60 |
| WF (control) | 25 | 60 | 60 min | 100 |
| Prot1/A-gal | 25 | 60 | 60 min | 52 |
| WF (control) | 50 | 65 | 60 min | 100 |
| Prot1/A-gal | 50 | 65 | 60 min | 59 |
| WF (control) | 25 | 65 | 60 min | 100 |
| Prot1/A-gal | 25 | 65 | 60 min | 33 |
| WF (control) | 50 | 50 | 120 min | 100 |
| Prot1/A-gal | 50 | 50 | 120 min | 78 |
| WF (control) | 25 | 50 | 120 min | 100 |
| Prot1/A-gal | 25 | 50 | 120 min | 56 |
| WF (control) | 50 | 60 | 120 min | 100 |
| Prot1/A-gal | 50 | 60 | 120 min | 58 |
| WF (control) | 25 | 60 | 120 min | 100 |
| Prot1/A-gal | 25 | 60 | 120 min | 33 |
| WF (control) | 50 | 65 | 120 min | 100 |
| Prot1/A-gal | 50 | 65 | 120 min | 56 |
| WF (control) | 25 | 65 | 120 min | 100 |
| Prot1/A-gal | 25 | 65 | 120 min | 28 |

As can be deduced from Table 2, all the enzyme based treatments, except the samples having the highest dry-matter content (50% w/w) and treated at the lowest temperature 50° C., show a reduction in residual trypsin inhibitor activity of >40%. The protease treatment might be added together with an alpha-galactosidase to reduce the carbohydrate based inhibitors like stacchyose and raffinose and to increase the utilization of energy content. As the two enzymes have distinctly different specificities no significant synergistic effect is expected.

Example 3

Test of Two Other Fungal Trypsin Like Proteases

Inactivation of trypsin inhibitor activity by two other fungal trypsin-like proteases from *Fusarium* species has been tested and compared to Prot1 used in the previous examples.

The enzymes used were:

Mature fungal trypsin-like endopeptidase from *Fusarium oxysporum*, Prot1. The amino acid sequence of such endopeptidase (translation product) is shown as SEQ ID NO: 1 of the present application.

Mature fungal trypsin-like endopeptidase from *Fusarium solani*, Prot2. The amino acid sequence of such endopeptidase (translation product) is shown as SEQ ID NO: 2 of the present application.

Mature fungal trypsin-like endopeptidase from *Fusarium sp.*, Prot3. The amino acid sequence of such endopeptidase (translation product) is shown as SEQ ID NO: 3 of the present application.

1000 µl of a 5% suspension of white flakes (50 mg/ml in Milli Q water, resulting pH of 6.5) was mixed with 50 µl enzyme solution in an Eppendorf tube and incubated 2 hours in an Eppendorf thermomixer at 50, 60 or 70° C. with vigorous shaking. A reference with Milli Q water added instead of enzyme solution was included. The proteases were dosed to give concentrations of 250 and 500 µg protease per g of soy protein (250 and 500 ppm).

Determination of trypsin inhibition and calculation of residual inhibitor activity (RIA) was done as in Example 1.

It has been verified that the contribution from the fungal trypsin-like proteases on the measured trypsin activity is negligible.

Results:

In Table 3 below, residual inhibitor activity results are given. It is seen that at a given enzyme dose Prot1 is inactivating the inhibitors more efficiently than either of Prot2 or Prot3 although these enzymes also give significant reduction in inhibitor activity relative to reference samples without protease added.

TABLE 3

Residual inhibitor activity (RIA) assay with results in % relative to reference at 50° C.

| RIA (%) | Prot1 500 ppm | Prot1 250 ppm | Prot3 500 ppm | Prot3 250 ppm | Prot2 500 ppm | Prot2 250 ppm | Reference |
|---|---|---|---|---|---|---|---|
| 50° C. | 75 | 95 | 84 | 102 | 102 | 121 | 100 |
| 60° C. | 24 | 37 | 37 | 47 | 65 | 80 | 92 |
| 70° C. | 28 | 41 | 41 | 63 | 36 | 47 | 70 |

Example 4

Comparison of Trypsin-Like Endopeptidase from *Fusarium oxysporum* (Prot1) with Alcalase and *Nocardiopsis* Protease Inactivation of trypsin inhibitor activity by Alcalase (available from Novozymes NS) and *Nocardiopsis* endopeptidase (from *Nocardiopsis* sp. NRRL 18262, previously described in, e.g., WO 88/03947, DNA and amino acid sequences previously published in, e.g., DK patent application no. 1996 00013) has been tested and compared to that of trypsin-like endopeptidase from *Fusarium oxysporum* (Prot1).

1000 µl of a 5% suspension of white flakes (50 mg/ml in Milli Q water, resulting pH of 6.5) was mixed with 50 µl enzyme solution in an Eppendorf tube and incubated 2 hours in an Eppendorf thermomixer at 60 or 70° C. with vigorous shaking. At each temperature a sample with Milli Q water added instead of enzyme was included. The proteases were dosed to give a concentration of 250 µg protease per g of soy protein (250 ppm).

Determination of trypsin inhibition and calculation of residual inhibitor activity (RIA) was done as in Example 1.

It has been verified that the contribution from Prot1, Nocardiopsis protease and Alcalase on the measured trypsin activity is negligible.

Results:

In Table 4 below, residual inhibitor activity results are given. It is seen that both at 60 and 70° C., trypsin-like *Fusarium* endopeptidase is inactivating the inhibitors more efficiently than either Alcalase or the *Nocardiopsis* endopeptidase.

TABLE 4

Residual inhibitor activity (RIA) assay with results in % relative to a reference (no enzyme) kept at room temperature

| RIA (%) | Prot1 | Nocardiopsis protease | Alcalase | No enzyme |
|---|---|---|---|---|
| 60° C. | 13 | 43 | 40 | 66 |
| 70° C. | 31 | 39 | 38 | 50 |

The invention claimed is:

1. A method of producing an enzyme-modified soybean product comprising treating an aqueous slurry of soybean flakes with a microbial proteolytic enzyme having specificity for arginine and/or lysine, wherein the enzyme-modified soybean product has a residual trypsin inhibitor activity which is at least 30% lower than a soybean product produced by the same method without addition of the microbial proteolytic enzyme and wherein the microbial proteolytic enzyme has an identity of at least 95% to amino acids 25-248 of SEQ ID NO: 1.

2. The method of claim 1, wherein the microbial proteolytic enzyme has an identity of at least 98% to amino acids 25-248 of SEQ ID NO: 1.

3. The method of claim 1, wherein the microbial proteolytic enzyme comprises the sequence of amino acids 25-248 of SEQ ID NO: 1.

4. The method of claim 1, further comprising grinding the soybean flakes prior to the treatment with the microbial proteolytic enzyme.

5. The method of claim 1, wherein at least 50% (w/w) of the soybean flakes to be enzyme treated will be retained on a No. 100 mesh (US standard) screen.

6. The method of claim 1, wherein the soybean flakes are subjected to defatting by solvent extraction before the enzyme treatment.

7. The method of claim 1, wherein the treatment is performed at a pH between 6 and 7.

8. The method of claim 1, wherein the aqueous slurry of soybean flakes has a dry matter content of at least 10%.

9. The method of claim 1, wherein the enzyme-modified soybean product is a feed or feed additive.

10. The method of claim 1, wherein the soybean flakes to be enzyme treated have not been heated to a temperature of 70° C. or above in the presence of more than 20% (w/w) water.

11. The method of claim 1, wherein the enzyme-modified soybean product has a residual trypsin inhibitor activity which is at least 40% lower than a soybean product produced by the same method without addition of the microbial proteolytic enzyme.

12. The method of claim 1, wherein the enzyme-modified soybean product has a residual trypsin inhibitor activity which is at least 50% lower than a soybean product produced by the same method without addition of the microbial proteolytic enzyme.

13. The method of claim 1, wherein the enzyme-modified soybean product has a residual trypsin inhibitor activity which is at least 60% lower than a soybean product produced by the same method without addition of the microbial proteolytic enzyme.

14. A method of producing an enzyme-modified soybean meal comprising
   (a) defatting soybean flakes by solvent extraction;
   (b) grinding the defatted soybean flakes to a soybean meal; and
   (c) treating an aqueous slurry of the soybean meal with a microbial proteolytic enzyme having specificity for arginine and/or lysine, wherein the microbial proteolytic enzyme has an identity of at least 95% to amino acids 25-248 of SEQ ID NO: 1;
wherein step (b) is performed before or after step (c).

15. The method of claim 14, wherein the microbial proteolytic enzyme has an identity of at least 98% to amino acids 25-248 of SEQ ID NO: 1.

16. The method of claim 14, wherein the microbial proteolytic enzyme comprises the sequence of amino acids 25-248 of SEQ ID NO: 1.

* * * * *

SEQUENCE LISTING

<160> NUMBER OF SEQ ID NOS: 3

<210> SEQ ID NO 1
<211> LENGTH: 248
<212> TYPE: PRT
<213> ORGANISM: Fusarium oxysporum

<400> SEQUENCE: 1

Met Val Lys Phe Ala Ser Val Val Ala Leu Val Ala Pro Leu Ala Ala
1               5                   10                  15

Ala Ala Pro Gln Glu Ile Pro Asn Ile Val Gly Gly Thr Ser Ala Ser
                20                  25                  30

Ala Gly Asp Phe Pro Phe Ile Val Ser Ile Ser Arg Asn Gly Gly Pro
            35                  40                  45

Trp Cys Gly Gly Ser Leu Leu Asn Ala Asn Thr Val Leu Thr Ala Ala
    50                  55                  60

His Cys Val Ser Gly Tyr Ala Gln Ser Gly Phe Gln Ile Arg Ala Gly
65                  70                  75                  80

Ser Leu Ser Arg Thr Ser Gly Gly Ile Thr Ser Ser Leu Ser Ser Val
                85                  90                  95

Arg Val His Pro Ser Tyr Ser Gly Asn Asn Asn Asp Leu Ala Ile Leu
                100                 105                 110

Lys Leu Ser Thr Ser Ile Pro Ser Gly Gly Asn Ile Gly Tyr Ala Arg
            115                 120                 125

Leu Ala Ala Ser Gly Ser Asp Pro Val Ala Gly Ser Ser Ala Thr Val
    130                 135                 140

Ala Gly Trp Gly Ala Thr Ser Glu Gly Gly Ser Ser Thr Pro Val Asn
145                 150                 155                 160

Leu Leu Lys Val Thr Val Pro Ile Val Ser Arg Ala Thr Cys Arg Ala
                165                 170                 175

Gln Tyr Gly Thr Ser Ala Ile Thr Asn Gln Met Phe Cys Ala Gly Val
            180                 185                 190

Ser Ser Gly Gly Lys Asp Ser Cys Gln Gly Asp Ser Gly Gly Pro Ile
    195                 200                 205

Val Asp Ser Ser Asn Thr Leu Ile Gly Ala Val Ser Trp Gly Asn Gly
        210                 215                 220

Cys Ala Arg Pro Asn Tyr Ser Gly Val Tyr Ala Ser Val Gly Ala Leu
225                 230                 235                 240

Arg Ser Phe Ile Asp Thr Tyr Ala
                245

<210> SEQ ID NO 2
<211> LENGTH: 251

```
<212> TYPE: PRT
<213> ORGANISM: Fusarium solani

<400> SEQUENCE: 2

Met Val Lys Phe Ala Ala Ile Leu Ala Leu Val Ala Pro Leu Val Ala
1               5                   10                  15

Ala Arg Pro Gln Asp Ser Ser Pro Met Ile Val Gly Gly Thr Ala Ala
            20                  25                  30

Ser Ala Gly Asp Phe Pro Phe Ile Val Ser Ile Ala Tyr Asn Gly Gly
        35                  40                  45

Pro Trp Cys Gly Gly Thr Leu Leu Asn Ala Asn Thr Val Met Thr Ala
    50                  55                  60

Ala His Cys Thr Gln Gly Arg Ser Ala Ser Ala Phe Gln Val Arg Ala
65                  70                  75                  80

Gly Ser Leu Asn Arg Asn Ser Gly Gly Val Thr Ser Val Ser Ser
                85                  90                  95

Ile Arg Ile His Pro Ser Phe Ser Ser Ser Thr Leu Asn Asn Asp Val
                100                 105                 110

Ser Ile Leu Lys Leu Ser Thr Pro Ile Ser Thr Ser Ser Thr Ile Ser
            115                 120                 125

Tyr Gly Arg Leu Ala Ala Ser Gly Ser Asp Pro Val Ala Gly Ser Asp
    130                 135                 140

Ala Thr Val Ala Gly Trp Gly Val Thr Ser Gln Gly Ser Ser Ser Ser
145                 150                 155                 160

Pro Val Ala Leu Arg Lys Val Thr Ile Pro Ile Val Ser Arg Thr Thr
                165                 170                 175

Cys Arg Ser Gln Tyr Gly Thr Ser Ala Ile Thr Thr Asn Met Phe Cys
            180                 185                 190

Ala Gly Leu Ala Glu Gly Gly Lys Asp Ser Cys Gln Gly Asp Ser Gly
        195                 200                 205

Gly Pro Ile Val Asp Thr Ser Asn Thr Val Ile Gly Ile Val Ser Trp
    210                 215                 220

Gly Glu Gly Cys Ala Gln Pro Asn Leu Ser Gly Val Tyr Ala Arg Val
225                 230                 235                 240

Gly Ser Leu Arg Thr Tyr Ile Asp Gly Gln Leu
                245                 250

<210> SEQ ID NO 3
<211> LENGTH: 250
<212> TYPE: PRT
<213> ORGANISM: Fusarium sp.

<400> SEQUENCE: 3

Met Val Lys Phe Ala Ala Ile Leu Ala Leu Val Ala Pro Leu Val Ala
1               5                   10                  15

Ala Arg Pro Gln Asp Arg Pro Met Ile Val Gly Gly Thr Ala Ala Ser
            20                  25                  30

Ala Gly Asp Phe Pro Phe Ile Val Ser Ile Ala Tyr Asn Gly Gly Pro
        35                  40                  45

Trp Cys Gly Gly Thr Leu Leu Asn Ala Ser Thr Val Leu Thr Ala Ala
    50                  55                  60

His Cys Thr Gln Gly Arg Ser Ala Ser Ala Phe Gln Val Arg Ala Gly
65                  70                  75                  80

Ser Leu Asn Arg Asn Ser Gly Gly Val Thr Ser Ala Val Ser Ser Ile
                85                  90                  95
```

-continued

```
Arg Ile His Pro Ser Phe Ser Gly Ser Thr Leu Asn Asn Asp Val Ser
            100                 105                 110

Ile Leu Lys Leu Ser Thr Pro Ile Ser Thr Ser Ser Thr Ile Ser Tyr
        115                 120                 125

Gly Arg Leu Ala Ala Ser Gly Ser Asp Pro Ala Ala Gly Ser Asp Ala
        130                 135                 140

Thr Val Ala Gly Trp Gly Val Thr Ser Gln Gly Ser Ser Ser Ser Pro
145                 150                 155                 160

Val Ala Leu Arg Lys Val Thr Ile Pro Ile Val Ser Arg Thr Thr Cys
                165                 170                 175

Arg Ser Gln Tyr Gly Thr Ser Ala Ile Thr Thr Asn Met Phe Cys Ala
            180                 185                 190

Gly Leu Ala Glu Gly Gly Lys Asp Ser Cys Gln Gly Asp Ser Gly Gly
        195                 200                 205

Pro Ile Val Asp Thr Ser Asn Thr Val Ile Gly Ile Val Ser Trp Gly
        210                 215                 220

Glu Gly Cys Ala Gln Pro Asn Phe Ser Gly Val Tyr Ala Arg Val Gly
225                 230                 235                 240

Ser Leu Arg Ser Tyr Ile Asp Gly Gln Leu
            245                 250
```